(12) United States Patent
Fernandez Rondan et al.

(10) Patent No.: US 11,420,060 B2
(45) Date of Patent: Aug. 23, 2022

(54) METHOD FOR TREATING EPISODES OF APNOEA AND/OR HYPOPNEA AND SYSTEM FOR DETECTING SAID EPISODES

(71) Applicant: TORYTRANS, S.L., Almagro (ES)

(72) Inventors: Baldomero Fernandez Rondan, Almagro (ES); Victor Javier Montero Blasco, Almagro (ES)

(73) Assignee: TORYTRANS, S.L., Almagro (ES)

( * ) Notice: Subject to any disclaimer, the term of this patent is extended or adjusted under 35 U.S.C. 154(b) by 121 days.

(21) Appl. No.: 16/637,528

(22) PCT Filed: Aug. 9, 2017

(86) PCT No.: PCT/ES2017/070574
§ 371 (c)(1),
(2) Date: Feb. 7, 2020

(87) PCT Pub. No.: WO2019/030419
PCT Pub. Date: Feb. 14, 2019

(65) Prior Publication Data
US 2020/0254250 A1 Aug. 13, 2020

(51) Int. Cl.
*A61N 1/36* (2006.01)
*A61B 5/08* (2006.01)
*A61B 5/087* (2006.01)

(52) U.S. Cl.
CPC .......... *A61N 1/3611* (2013.01); *A61B 5/0826* (2013.01); *A61B 5/0878* (2013.01); *A61B 2562/0204* (2013.01); *A61B 2562/0247* (2013.01); *A61N 1/36175* (2013.01)

(58) Field of Classification Search
None
See application file for complete search history.

(56) References Cited

U.S. PATENT DOCUMENTS

| 8,545,416 | B1 | 10/2013 | Kayyali et al. |
| 9,186,511 | B2* | 11/2015 | Bolea .................. A61N 1/0556 |
| 2014/0194793 | A1 | 7/2014 | Nakata et al. |
| 2016/0262637 | A1 | 9/2016 | Delia |
| 2017/0196760 | A1 | 7/2017 | Hyde et al. |

FOREIGN PATENT DOCUMENTS

| EP | 2810599 A1 | 12/2014 |
| WO | 2013113950 A1 | 8/2013 |
| WO | 2014165834 A1 | 10/2014 |

OTHER PUBLICATIONS

International Search Report for Corresponding International Application No. PCT/ES2017/070574 (3 Pages)(dated Apr. 19, 2018).

* cited by examiner

*Primary Examiner* — Michael W Kahelin
*Assistant Examiner* — Elizabeth K So
(74) *Attorney, Agent, or Firm* — Lucas & Mercanti, LLP

(57) ABSTRACT

A method for treating episodes of apnoea and/or hypopnea is provided. The method has the steps of: a) detecting or predicting an episode of apnoea and/or hypopnea by means of at least one sensor selected from a respiratory pressure sensor, a pulse oximeter, an acoustic sensor and/or a respiratory temperature sensor; and b) emitting an electrical signal by means of an electrical actuator connected to at least one submental nerve and/or muscle, the electrical signal having a bipolar waveform and a frequency between 5 and 100 Hz.

6 Claims, 5 Drawing Sheets

METHOD FOR TREATING EPISODES OF APNOEA AND/OR HYPOPNEA AND SYSTEM FOR DETECTING SAID EPISODES

CROSS REFERENCE TO RELATED APPLICATION

This Application is a 371 of PCT/ES2017/070574 filed on Aug. 9, 2017, which is incorporated herein by reference.

FIELD OF THE INVENTION

The present invention describes a method for treating obstructive sleep apnoea and/or hypopnea syndrome (hereinafter, OSAHS) which is particularly advantageous when used before an episode of apnoea and/or hypopnea occurs or at the first signs of said episode. Additionally, the present invention describes a system which allows the predictive detection of episodes of apnoea and/or hypopnea to preferably be used with said method.

The present invention describes a portable, wearable, non-invasive system that does not require surgical intervention, which allows treating in real time a user who presents episodes of apnoea and/or hypopnea, and preferably determining whether an episode of apnoea and/or hypopnea will occur in order to proceed to treat said episode in real time.

BACKGROUND OF THE INVENTION

OSAHS (Obstructive Sleep Apnoea/Hypopnea Syndrome) is currently under-diagnosed and under-treated. Undiagnosed patients consume many more health resources than those who, while suffering OSAHS, are correctly diagnosed and treated. This has turned OSAHS into a major public health issue.

The reference test for diagnosing OSAHS is a polysomnography, but it is a long, complex and expensive test that requires skilled medical personnel.

Additionally, several invasive systems have been developed for, after detecting the syndrome, unilaterally stimulating the hypoglossal nerve (HGN) for patients with moderate to severe OSAHS by means of a neurostimulator which requires surgical intervention that lasts for about 140 minutes so it can be implanted in the infraclavicular region, coupled to an intercostal sensor for detecting the breathing effort and an electrode tunneled in to reach the submandibular region and electrically stimulate the HGN. The device is activated by the patient during sleep and discharges are produced with every breathing effort that is detected, regardless of whether or not apnoea and/or hypopnea are taking place.

In turn, Schwartz et al. (Schwartz A R, Barnes M, Hillman D, Malhotra A, Kezirian E, Smith PL et al. Acute upper airway responses to hypoglossal nerve stimulation during sleep in obstructive sleep apnea. Am J Respir Crit Care Med. 2012 Feb. 15; 185(4):420-6.) describes the effect of the incremental stimulation of the HGN synchronised with alternating inspirations in 30 patients with SAHS. The peak inspiratory flow and the limitation to inspiratory flow between stimulated and non-stimulated inspirations were compared for each stimulation level. A pronounced increase in peak inspiratory flow without causing arousal of subjects was demonstrated; however, a clear drop in the obstruction of flow to the pharynx could not be objectified.

In addition to said invasive systems, the applicant of the present invention described in patent EP2810599 a non-invasive device and method for detecting episodes of apnoea and/or hypopnea. However, said invention relates to detecting said episodes of apnoea and/or hypopnea by means of acoustic signal analysis once the episode has taken place. Therefore, it lacks the capacity to predict a future episode to prevent said episode from taking place.

DESCRIPTION OF THE INVENTION

To solve the problems of the prior art, the present invention describes a method for treating episodes of apnoea and/or hypopnea, which comprises the steps of:
  a. detecting or predicting an episode of apnoea and/or hypopnea by means of at least one sensor selected from a respiratory pressure sensor, a pulse oximeter, an acoustic sensor and/or a respiratory temperature sensor;
  b. emitting an electrical signal by means of an electrical actuator connected to at least one submental nerve and/or muscle;
wherein said electrical signal has a bipolar waveform and a frequency between 5 Hz and 100 Hz.

In a preferred embodiment, the bipolar wave comprises a positive cycle and a negative cycle, additionally, in one example, one of the cycles has a maximum value which is 40% greater than the maximum value of the other cycle. Additionally, the bipolar wave may comprise a delay between cycles of between 0 and 10 ms. In terms of the bipolar wave intensities, the present invention contemplates a particular embodiment in which said peak-to-peak intensity is in a range between 1 and 20 mA Preferably, the step for a predictive detection of the episode of apnoea and/or hypopnea. A predictive detection in the context of the present invention refers to identifying the event before it occurs, i.e., in the proximity of the occurrence of an episode. The detection can be performed, for example, by means of at least one pressure sensor which quantifies the respiratory signal and the storage in a memory of historical values of the respiratory signal, and by comparing the current values with historical values. A processor can subsequently be used to use said comparisons with historical values to determine the possibility an episode of apnoea or hypopnea occurring.

Preferably, the historical values of the respiratory signal comprise a statistical value of the latest measurements.

Moreover, the present invention describes a system for predicting episodes of apnoea and/or hypopnea characterised in that it comprises:
  At least one respiratory signal sensor;
  A memory arranged for storing a series of respiratory signal measurements and a temporary identification of each of the measurements; and
  A processor connected to the memory for accessing the series of measurements and to the respiratory pressure sensor so as to access the current measurement;
wherein the processor has comparison means for comparing the data series and the current measurement, determination means for determining a reduction of the current measurement below a threshold level stored in the memory and emission means for emitting a treatment signal if the reduction is below the threshold level.

As in the case of the method, the pressure sensor can be a sensor selected from a pressure sensor, a temperature sensor, a pulse oximeter, an acoustic sensor and/or a flow sensor.

In a preferred embodiment, the threshold is a dynamic threshold, i.e., the threshold can be modified based on earlier parameters and can, for example, be automatically adjusted to the parameters of each user, i.e., the dynamic threshold can be determined by means of the statistical comparison of a series of measurements of the series.

In a preferred embodiment, the system has at least one additional sensor selected from the group formed by a pulse oximeter, an electromyography sensor, a temperature sensor, a motion sensor and an audio sensor.

Additionally, in addition to the respiratory pressure measurements, it is possible to store in the memory measurements corresponding to at least one additional sensor.

In a particularly preferred embodiment, the processor has correlation means for correlating the respiratory pressure sensor and the at least one sensor. Furthermore, the processor may comprise correlation means for correlating the measurements of the pressure sensor and the measurements of the at least one sensor stored in the memory. Preferably, the correlation means comprise means of artificial intelligence, in this case, said means may be previously trained to predict a reduction below the threshold level and comprise emission means for emitting the treatment signal.

In a particular embodiment, the system is a portable system.

Optionally, the reduction of the current measurement is calculated considering historical measurements, for example at least the measurements corresponding to the last 10 seconds or according to the medical criteria established in each case.

One of the advantages of the device according to the present invention is the capacity to perform suitable diagnosis and treatment by means of a system that lacks invasive sensors.

In terms of the treatment of the episodes once they are detected, the present invention contemplates the treatment signal being sent to an actuator. The actuator may comprise, for example, at least two electrodes. Said electrodes can be arranged to act on the submental morphology associated with OSAHS.

As in the case of the method of the present invention, the treatment signal comprises a pulse having a positive cycle and a negative cycle. The negative cycle preferably has an area substantially equal to the area of the negative cycle, although in particular embodiments of the present invention at least one of the cycles has a signal with an amplitude 40% greater than in the other cycle. Furthermore, the treatment signal can be a pulse train.

The present invention furthermore describes a method for detecting episodes of apnoea and/or hypopnea, characterised in that it comprises the steps of:

i) Measuring the respiratory signal of a user by means of at least one pressure sensor measuring pressure variations;
ii) Storing in a memory a series of measurements including a temporary identification of each measurement;
iii) Comparing the measurement obtained in step i) with at least one measurement obtained from the memory;
iv) Calculating the reduction of the current measurement based on the comparison of step iii);
v) Determining an episode of apnoea and/or hypopnea if the reduction calculated in step iv) is below a threshold level stored in the memory.

BRIEF DESCRIPTION OF THE DRAWINGS

The attached figures show an embodiment of the system according to the present invention in an illustrative and non-limiting manner, in which.

DETAILED DESCRIPTION OF AN EMBODIMENT

Figure 1:
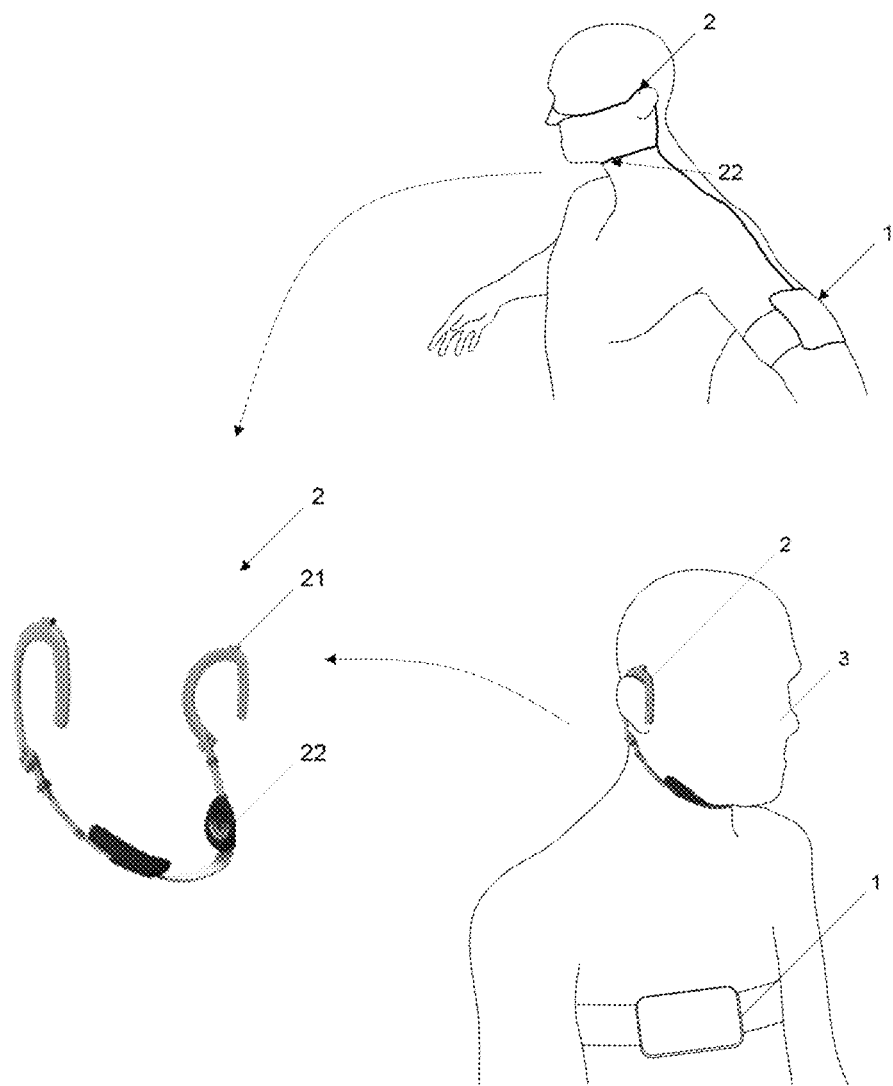
FIG. 1 shows an embodiment of a system for detecting and treating apnoea and/or hypopnea according to the present invention.

FIG. 1 shows a preferred embodiment of a system according to the present invention, wherein the system has a sensing module (1) comprising at least one sensor of the respiratory signal of the user in which said sensor is, for example, a pressure sensor measuring the amplitude of the respiratory signal. Furthermore, said sensor is disposed, for example, by means of a cannula, in the nasal cavity of the user, and furthermore there is a sensing module placed on the arm or chest of the patient (3), or anywhere else.

The pressure sensor measures the respiratory signal of the user (3) by the highly sensitive detection of pressure variations. Disruptions from the environment are thereby prevented, and higher reliability of the detection of the respiratory signal is achieved. Examples of said respiratory signal sensors can be based on pressure, temperature and/or flow sensors. In any case, the objective is to determine the characteristics of the breathing of the user.

Moreover, the system has an actuator (2) with means for being attached to the user (3). In the example of FIG. 1, the actuator (2) has side pieces (21) for being arranged around the ears of the user (3). The actuator further comprises electrodes (22) for acting non-invasively on at least one muscle and/or a nerve of the morphology connected to the airway of the user, for example, a submental muscle connected to the airways.

Additionally, the system has a processor with the capacity to communicate with the sensing module (1) and the actuator (3), which will be explained in further detail in reference FIG. 2.

Figure 2:
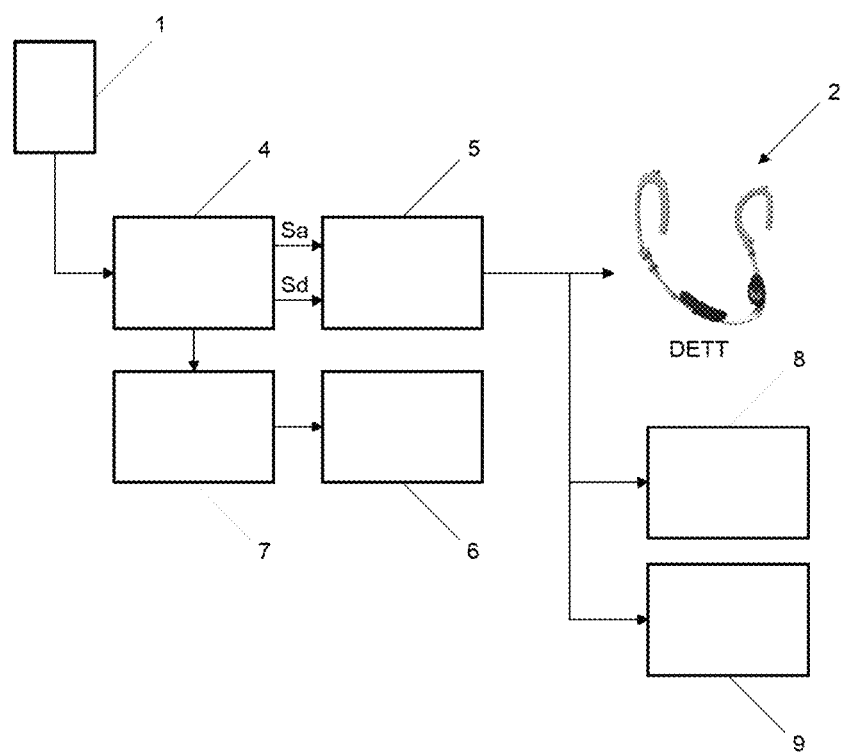
FIG. 2 shows a modular schematic view of an example of a system according to the present invention.

FIG. 2 shows a schematic view in which there is provided a processor incorporating a memory and data processing means. The sensing module (1) is provided as input to said processor and a signal is provided as output to the actuator (2) for the processing of the signals, to a display module (8) or to a memory (9) where data relating to the emitted output signals can be stored. The means for the communication of the processor with the actuator are preferably cables, and the means for the communication with the sensing module are preferably cables, although completely wireless and partially wired and/or wireless configurations are also contemplated in the present invention.

In terms of the sensing module (1), it may comprise additional sensors which allow improving an eventual prediction/detection of an episode of apnoea and/or hypopnea. Namely, it is contemplated that the following additional sensors can be provided:

Temperature sensor: Allows measuring airflow temperature variations, which data can be used complementarily or alternatively to the respiratory signal data. This variable provides additional information in order to use it if required in recording variables of patients in some circumstances. A body temperature sensor would measure the body temperature of the patient should one be arranged.

Pulse oximeter sensor: Allows measuring the heart rate and blood oxygen saturation. This measurement improves the diagnostic parameters so as to improve, along with other variables, the detection of episodes of apnoea and/or hypopnea in some cases. This measurement is usually performed non-invasively by means of optical sensors.

Electromyography sensor: Allows measuring muscle tone in the region of the neck relating to the muscles connected to the airway. It is useful for monitoring the state of the airways of the patient for self-adaptation of the stimulation signals to the characteristics and situation of the patient, mainly in the therapeutic training mode.

Position and motion sensor: Allows determining the position and motion of a patient, for example by means of a three-dimensional inertial sensor by means of an IMU (Inertial Measurement Unit) or by means of an accelerometer, and provides additional data for establishing the processing of the information for diagnosis, taking into account the mobility and position of the patient at the time of detecting the episode and throughout his or her entire sleep cycle.

Acoustic sensor: Allows improving the detection of snoring and respiratory sounds and provides additional data about apnoea and/or hypopnea. It can be used in certain circumstances to relate it to other variables.

Subsequently, the signals coming from the sensors to be used are sent to the processor and, namely, to an event detection module (4), in which said module analyses the current signals with respect to earlier signals stored in a memory.

Namely, the event detection module is provided with a memory in which the signals coming from the sensing module (1) are stored together with data related to the moment when the measurements are taken, for example, the time or a temporal reference type. Subsequently, the module analyses the current data received directly from the sensing module (1), and by means of comparison means, compares the earlier data series with the current measurement for, subsequently, by means of determination means, calculating whether there is a reduction of the current measurement of the respiratory signals below a threshold level stored in the memory. It also has emission means for emitting a treatment signal if the reduction is below the threshold level. Said event detection module can be updated in real or quasi-real time with respect to the measurements performed in the user.

If it is determined that there is a reduction below a threshold level during a given time, this means that the user will soon experience an episode of apnoea and/or hypopnea, therefore in an exemplary embodiment, the actual event is stored in an event recording module (7). Said thresholds can be predetermined thresholds or they can be defined by means of a calibration method so as to adapt them to the user, and additionally, said detection thresholds can be automatically adapted taking into account earlier measurements and can be adapted to the characteristics of the patient, for example, by means of artificial intelligence algorithms.

Alternatively, the system can have an actuator (2) which exerts on the user, through non-invasive means, an action, for example, to stimulate the morphology involved in OSAHS. Accordingly, the processor can have a stimulus generation module (5), where the stimuli can be, for example, signals controlling an electric generator connected to the actuator and electrodes for stimulating the morphology involved in OSAHS. Moreover, said outputs of the stimulus generation module can also be sent to a screen (8) to be displayed in real time and/or stored in an event memory (9).

Additionally, the system can have a remote transmission module (6) which allows transmitting, for example, the data stored in the event recording module (7) to a remote server such as the server of a medical service.

Figure 3:
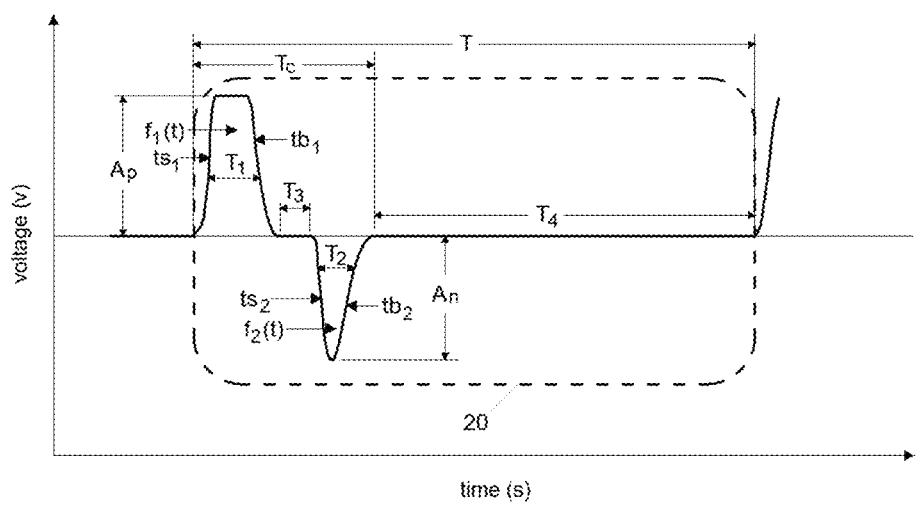
FIG. 3 shows an example of a standard pulse of a treatment signal according to the present invention.

FIG. 3 shows an exemplary embodiment of a standard pulse (20) for a treatment signal according to the present invention. Namely, the signal of FIG. 3 shows the waveform of the standard pulse (20) which contains a positive part of amplitude (Ap), a time of duration at half its amplitude ($T_1$) and a form according to the temporal function ($f_1(t)$); it furthermore has a negative part of amplitude (An), a time of duration at half its amplitude ($T_2$) and a form according to the temporal function ($f_2(t)$).

Additionally, the standard pulse (20) can have a period of the standard pulse signal or time between repetitive pulses (T), a time between positive pulse and negative pulse ($T_3$), a cycle time of the positive and negative standard pulse ($T_c$), a pulse-free time at level zero between cycles of the standard pulse ($T_4$), a positive pulse rise time ($ts_1$), a positive pulse decay time ($tb_1$), a rise time of the negative pulse (ts2) and a decay time of the negative pulse (tb2).

The form of the standard pulse (20) may comprise of a positive wave section and a negative wave section with the times in zero state distributed such that it has a symmetrical effect; said configuration is particularly advantageous because, since it is sent to an electrode to act on the submental morphology, it generates significant opening of the airways, and prevents uncomfortable involuntary movement gestures of the lips and chin when the stimulation signal is received.

The intensity levels and frequency of the pulses are designed to produce the desired depth effect of the wave in order to reach the suitable muscle or nerve, and efficacy of the stimulation, and minimise the side effects of temperature increase of the skin and pain and unwanted gestures and movements.

Figure 4:
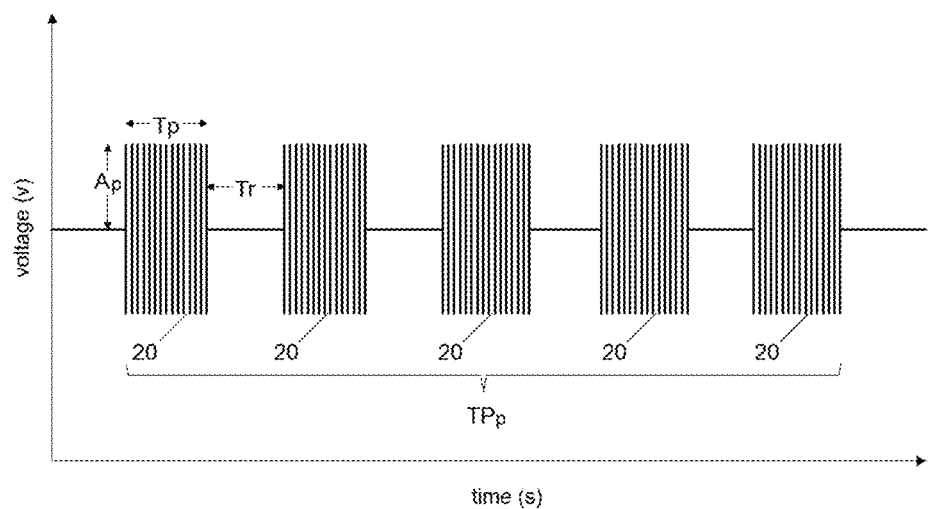
FIG. 4 shows an example of a treatment signal comprising a standard pulse train.

FIG. 4 shows an embodiment in which the treatment signal comprises a standard pulse train (TPp) which can be, for example, a continuous train of duration (Tp), of standard pulses (Pp), of amplitude (Ap) and relaxation time of the pulse train of duration (Tr). The duration of the pulse train is TPp.

In one embodiment, the treatment signal can be maintained continuous, but these interruptions of the standard pulse train could be applied, whereby providing an additional parameter for improving the efficacy of the stimulation.

Figure 5:
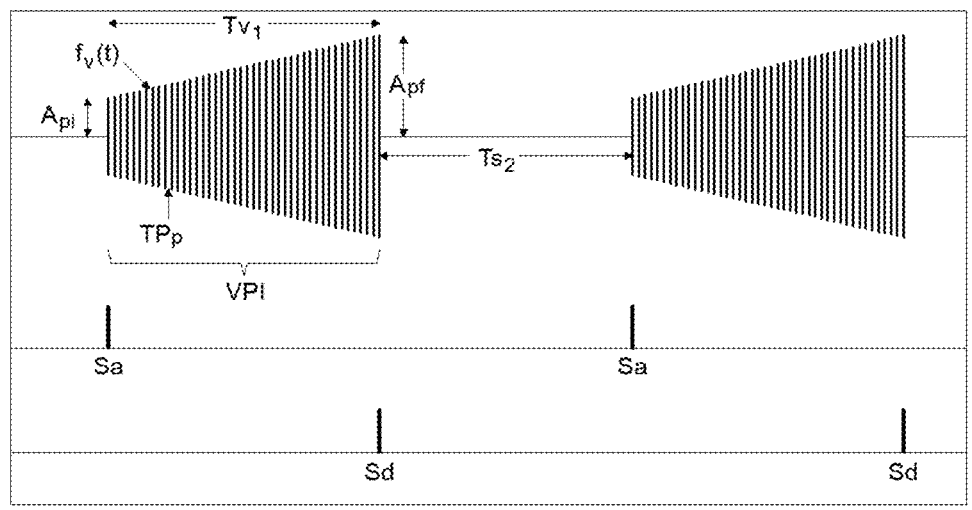
FIG. 5 shows another example of a treatment signal comprising a standard pulse train with variable intensity.

FIG. 5 depicts a particular embodiment of a treatment signal according to the present invention in which the form of the progressive variation in intensity of the stimulation wave (VPI) formed by standard pulse trains (TPp). The activation signal of the treatment wave (Sa) starts the stimulation process. It begins with standard pulse trains TPp with an initial amplitude (Api) which is less than the level necessary for causing the airway to open. This level can progressively increase until reaching the final amplitude of the stimulation wave (Apf). This final amplitude is determined by the resolution of the episode due to the sufficient opening of the airway occurring, which is detected by the sensors, or by reaching a safety threshold. At this time, the deactivation signal of the treatment wave (Sd) is generated, in which the initial and final amplitude thresholds are adjusted to the characteristics and state of the patient.

The incremental increase in the amplitude of the treatment signal is particularly relevant in that it allows starting a treatment with a low initial amplitude (Api). Therefore, if treatment is sufficient with said low amplitude and the episode of apnoea or hypopnea is solved, it is not necessary to increase the intensity of the signal. It is thereby ensured that the treatment is performed with the least action possible on the patient and with the lowest possible energy consumption.

In FIG. 5, the time of duration of each activation of the treatment wave ($Tv_1$) is determined by the final amplitude of the stimulation wave (Apf) described in the preceding paragraph.

The silence (signal-free) times of each activation of the stimulation wave ($Ts_2$) are determined by the time lapsing between the resolution of an episode and the detection of a new episode. In another embodiment of the present invention, the action and silence times and levels are determined by a training sequence.

The form of the envelopment of the progressive variation in intensity of the stimulation wave (VPI) of FIG. 5 has a temporal function Fv(t), which is usually a ramp function.

A table is shown below with the different episodes that can be detected and/or treated with a device according to the present invention. The table shows the values currently accepted by the medical community. Although the detection parameters are susceptible to changes, said changes in detection parameters can likewise be modified in a device according to the present invention in order to accommodate said changes in criterion.

| | |
|---|---|
| Obstructive apnoea | Absence or reduction >90% of the respiratory signal (thermistors, nasal cannula or pneumotachograph) of >10 seconds in duration in the presence of respiratory effort detected by the respiratory pressure sensors. |
| Central apnoea | Absence or reduction >90% of the respiratory signal of >10 seconds in duration in the absence of respiratory effort. |
| Mixed apnoea | A respiratory event which usually begins with a central component and ends in an obstructive component. |
| Hypopnea[a] | Discernible reduction (>30% and <90%) of the amplitude of the respiratory signal of >10 seconds in duration. |
| Respiratory effort-related micro-arousals (RERM) | Period >10 seconds of progressive increase in respiratory effort. It can also be detected by short flow limitation-flattening periods of the respiratory signal. |

Each of the treatment parameters must be calibrated with respect to the patient and calibration is performed by configuring the parameters such that they cause the least possible discomfort for the patient and open the airways.

In tests performed on actual subjects, this perception or discomfort is virtually nil, achieving a very significant opening of the airway. Accordingly, this achieves a benefit for the patient as it causes virtually nil discomfort.

The invention claimed is:

1. A method for treating episodes of apnoea and/or hypopnea of a user, which comprises the steps of:
   a. predicting an episode of apnoea and/or hypopnea of the user comprising:
      quantifying a current respiratory signal comprising:
         measuring a current respiratory pressure value by a respiratory pressure sensor, and
         measuring a current respiratory temperature value by a respiratory temperature sensor;
      comparing, by a processor, the measured current respiratory pressure value and measured current respiratory temperature value with corresponding thresholds, wherein each threshold is dynamic and is automatically modified based on historical measured values of the user, wherein the historical measured values are stored in a memory; and
   b. generating a stimulus comprising:
      emitting an electrical signal by an electrical actuator non-invasively connected to at least one submental nerve and/or muscle of the user,
   wherein the electrical signal has a bipolar waveform and a frequency between 5 Hz and 100 Hz;
   wherein the bipolar waveform comprises a positive cycle and a negative cycle, and
   wherein one of the positive and negative cycles has a maximum value which is 40% greater than the maximum value of the other positive and negative cycle.

2. The method according to claim 1, wherein the bipolar waveform comprises a delay between the positive cycle and the negative cycle of between 0 and 10 ms.

3. The method according to claim 1, wherein the electrical signal as a peak-to-peak intensity is between 1 and 20 mA.

4. The method according to claim 1, wherein the historical values of the respiratory signal comprise a statistical value of the latest measurements.

5. The method according to claim 1, wherein the step of quantifying the current respiratory signal further comprises measuring a heart rate and a blood oxygen saturation by a pulse oximeter.

6. The method according to claim 1, wherein quantifying the current respiratory signal further comprises measuring a respiratory sound by an acoustic sensor.

\* \* \* \* \*